United States Patent
Brinkmann et al.

(10) Patent No.: US 11,224,457 B2
(45) Date of Patent: Jan. 18, 2022

(54) CATHETER-BASED OCCLUSION REMOVAL SYSTEMS AND METHOD

(71) Applicant: W. L. Gore & Associates, Inc., Newark, DE (US)

(72) Inventors: John M. Brinkmann, Flagstaff, AZ (US); Paul D. Goodman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/759,656

(22) PCT Filed: Dec. 20, 2018

(86) PCT No.: PCT/US2018/066758
§ 371 (c)(1),
(2) Date: Apr. 27, 2020

(87) PCT Pub. No.: WO2019/126474
PCT Pub. Date: Jun. 27, 2019

(65) Prior Publication Data
US 2021/0169517 A1    Jun. 10, 2021

Related U.S. Application Data

(60) Provisional application No. 62/609,046, filed on Dec. 21, 2017.

(51) Int. Cl.
*A61B 17/3207* (2006.01)
*A61B 17/00* (2006.01)

(52) U.S. Cl.
CPC ........... *A61B 17/320758* (2013.01); *A61B 2017/00867* (2013.01); *A61B 2017/320716* (2013.01)

(58) Field of Classification Search
CPC ........ A61B 17/3207; A61B 17/320725; A61B 17/320758; A61B 2017/00685;
(Continued)

(56) References Cited

U.S. PATENT DOCUMENTS 6,025,044 A    2/2000    Campbell et al.
6,454,775 B1   9/2002    Demarais et al.
(Continued)

FOREIGN PATENT DOCUMENTS

JP    02-071509 A       3/1990
JP    2015-505250 A     2/2015
(Continued)

OTHER PUBLICATIONS

International Search Report and Written Opinion received for PCT Patent Application No. PCT/US2018/066758, dated Mar. 19, 2019, 13 pages.

*Primary Examiner* — George J Ulsh

(57) ABSTRACT

A catheter system (110) for removal of occlusive material in a body lumen. The catheter system (110) includes a catheter body (10), extending between a distal end (20) and a proximal end (22) and having a proximal portion (29) and a distal portion (28). The catheter body (10) includes a filtration section (30A) having filter media (32) configured to permit blood to pass through the lumen of the catheter body (10) and inhibiting occlusive material from passing out of the catheter body (10). The catheter system (110) also includes a control handle (120) coupled to the proximal portion (29) of the catheter body (10) and a cutter assembly (12) having a drive mechanism (40) operatively coupled to the control handle (120). The cutter assembly (12) includes a drive mechanism (40) and a conveyor (44) coupled to the drive mechanism (40) and rotatable with the drive mechanism (40) to convey occlusive material proximally within (Continued)

the catheter body (10) and through the filtration section (30A).

20 Claims, 4 Drawing Sheets

(58) Field of Classification Search
CPC .. A61B 2017/320716; A61B 2017/005; A61B 2217/007; A61B 2017/00867
See application file for complete search history.

(56) References Cited

U.S. PATENT DOCUMENTS

| | | |
|---|---|---|
| 8,900,257 B2 | 12/2014 | Straub et al. |
| 9,492,192 B2 | 11/2016 | To et al. |
| 9,545,300 B2 | 1/2017 | Cully et al. |
| 2001/0031981 A1* | 10/2001 | Evans .................. A61B 17/221 606/200 |
| 2003/0057156 A1* | 3/2003 | Peterson .......... A61B 17/12122 210/645 |
| 2003/0139751 A1 | 7/2003 | Evans et al. |
| 2003/0187495 A1 | 10/2003 | Cully et al. |
| 2004/0093012 A1 | 5/2004 | Cully et al. |
| 2007/0255252 A1 | 11/2007 | Mehta |
| 2009/0198219 A1 | 8/2009 | Campbell et al. |
| 2015/0223920 A1 | 8/2015 | Bruchman et al. |
| 2016/0213396 A1 | 7/2016 | Dowell et al. |

FOREIGN PATENT DOCUMENTS

| | | |
|---|---|---|
| JP | 2016-511106 A | 4/2016 |
| JP | 2016-513524 A | 5/2016 |
| WO | 01/74255 A1 | 10/2001 |
| WO | 02/71977 A2 | 9/2002 |
| WO | 2014/141226 A1 | 9/2014 |
| WO | 2014/150288 A2 | 9/2014 |
| WO | 2016/204137 A1 | 12/2016 |

\* cited by examiner

CATHETER-BASED OCCLUSION REMOVAL SYSTEMS AND METHOD

CROSS-REFERENCE TO RELATED APPLICATION

This application is a national phase application of PCT/US2018/066758, filed Dec. 20, 2018, which claims the benefit of Provisional Application No. 62/609,046, filed Dec. 21, 2017, which is incorporated herein by reference in its entirety for all purposes.

FIELD

The present disclosure relates generally to removal of unwanted debris or other material within a body lumen. More specifically, the present disclosure relates to catheter systems for the removal of occlusive material within a body lumen, and methods thereof.

BACKGROUND

Endovascular clearing procedures exist for the removal of blockages and restoration of blood flow through body lumen. Such procedures may be necessary as a result of various endovascular diseases. For example, peripheral artery disease (PAD) is a condition involving narrowing of an artery due to an accumulation of plaque. As plaque builds on the inner wall of the lumen, blood flow through the lumen and to the respective organ is restricted. If the lumen is not cleared, permanent occlusion and restriction of blood flow may occur, which can lead to more serious conditions such as necrosis. Other occlusive materials that may create similar blockages include thrombi (i.e. blood clots), fat globules, gas bubbles, and other foreign bodies within the blood stream. These types of foreign matter in the body are generally referred to in this disclosure as "occlusive materials," "occlusive debris," or "occlusive aggregate."

When performing various endovascular procedures, occlusive materials are removed from within body lumen to prevent blockages, embolization, and to restore adequate blood flow. Examples of such procedures include, for example, embolectomies and atherectomies in which occlusive materials are removed from arteries, veins, blood vessels, and other vasculature using a variety of removal techniques. Current techniques generally include maceration of the occlusive material via various devices designed to cut, shave, sand, grind or otherwise reduce the blockages. However, this often creates free-flowing occlusive debris within the body lumen, removal of which is often desired to prevent further, distal embolization. The devices may remove debris by trapping, filtering, or aspirating the occlusive debris from the blood stream. However, techniques such as these often result in significant blood loss for the patient and removal of occlusive debris without blood loss is difficult. Further, if significant amounts of occlusive debris remain in the blood stream, embolization may recur. Thus, there is a need for a device allowing occlusive debris removal from blood in-situ with minimal blood loss or risk of embolization.

SUMMARY

Various examples relate to an occlusion removal system including a catheter body, a control handle, and a cutter assembly. The cutter assembly includes a drive mechanism and a conveyor for conveying occlusive material from a body lumen through the catheter body. In various examples, the occlusion removal system facilitates removal of occlusive debris or other material from the body lumen without substantial loss of bodily fluid, such as blood, during the process.

According to one example ("Example 1"), an occlusion removal system includes a catheter body, a control handle coupled to a proximal portion of the catheter body, and a cutter assembly. The catheter body extends between a distal end and a proximal end and has a distal portion and a proximal portion. The distal portion includes a filtration section including filter media configured to permit blood to pass from the lumen of the catheter body and to inhibit occlusive material from passing out of the catheter body. The cutter assembly includes a drive mechanism extending between the proximal portion and distal portion of the catheter body and operatively coupled to the control handle. The cutter assembly also includes a conveyor extending within the distal portion of the catheter body. The conveyor is coupled to the drive mechanism such that the conveyor rotates with the drive mechanism to convey occlusive material from the body lumen proximally within the catheter body such that blood is permitted to pass from the lumen of the catheter body and the occlusive material is inhibited from passing out of the lumen of the catheter body and is conveyed proximally within the lumen of the catheter body.

According to another example ("Example 2") further to Example 1, the cutter assembly includes a cutter configured to cut occlusive material. The cutter extends from the distal end of the catheter body and is coupled to the drive mechanism such that the cutter is rotatable with the drive mechanism to cut occlusive material.

According to another example ("Example 3") further to Example 2, the cutter includes one or more burr elements and the conveyor includes one or more screw elements and/or impeller elements.

According to another example ("Example 4") further to any of Examples 1 to 3, the filter media includes ePTFE.

According to another example ("Example 5") further to any of Examples 1 to 4, the system also includes an outer sheath. The outer sheath has a lumen and is configured to extend over the filtration section such that fluid is deliverable through the lumen of the outer sheath to flush the occlusive material out of the cutter assembly by introducing the fluid into the lumen of the catheter body and rotating the conveyor.

According to another example ("Example 6") further to any of Examples 1 to 5, the filtration section defines a portion of the lumen of the catheter body. The conveyor contracts the filtration section to define spaces configured to trap the occlusive material between the conveyor and the filtration section as the occlusive material is conveyed within the catheter body.

According to another example ("Example 7") further to Example 2, the drive mechanism includes an electric motor and a shaft operatively coupling the electric motor to at least one of the conveyor and the cutter.

According to another example ("Example 8") further to any of Examples 1 to 7, the distal portion of the catheter body also includes an impermeable section between the distal end of the catheter body and the filtration section. The impermeable section is impermeable to fluid.

According to another example ("Example 9") further to any of Examples 1 to 8, the cutter assembly is self-expandable from a first diametric profile to a second, larger diametric profile to fit a body lumen.

According to another example ("Example 10") further to any of Examples 1 to 9, the cutter assembly includes a self-expanding frame formed of a shape-memory material.

According to another example ("Example 11"), a method of removing occlusive material from a body lumen includes intraluminally delivering a catheter system to a desired treatment site within the body lumen of a patient, activating rotation of a cutter assembly proximate an occlusive material in the body lumen at a speed adequate to produce a pressure drop, causing the occlusive material to be drawn into the distal end of the catheter body and conveyed proximally within the catheter body while blood is permitted to return to the body lumen through filter media within a filtration section as the occlusive material is conveyed proximally.

The foregoing Examples should not be read to limit or otherwise narrow the scope of any of the inventive concepts otherwise provided by the instant disclosure.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
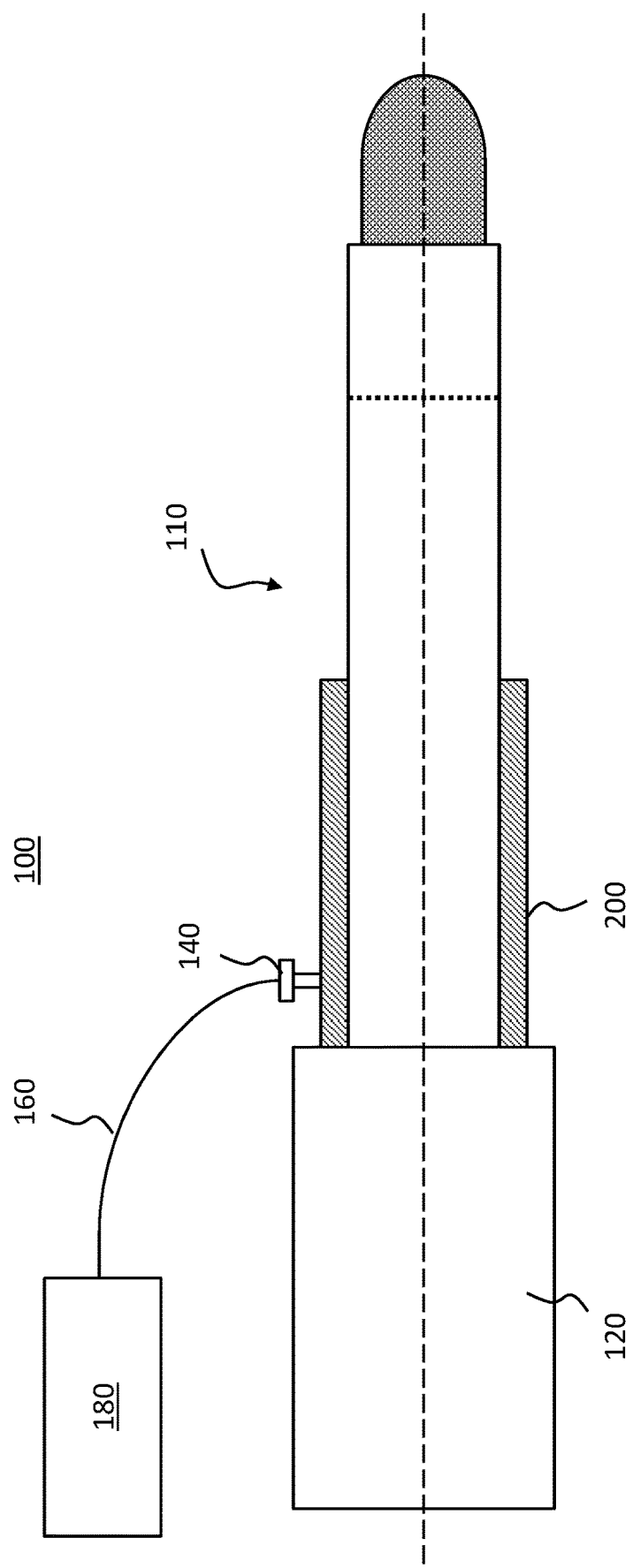
FIG. 1 shows an occlusion removal system, according to some embodiments.

FIG. 1 shows an occlusion removal system 100 for removal of occlusive material from within body lumen, according to some embodiments. Examples of body lumens in which the occlusion removal system 100 is employed include arteries, veins, airways, biliary system, gastrointestinal passages, and other body conduits. The occlusion removal system 100 includes a catheter system 110, a control handle 120, a valve 140, a delivery tube 160, and a fluid supply 180. As shown, the catheter system 110 is coupled to the control handle 120. The valve 140 is in communication with the catheter system 110 and, in one embodiment, can be located proximate the control handle 120. The delivery tube 160 is attached to the valve 140 and, at an opposite end, the fluid supply 180.

In various examples, the occlusion removal system 100 facilitates removal of occlusive debris or other material from the body lumen without substantial loss of bodily fluid, such as blood, during the process. For example, in a thrombosis or plaque removal operation, the occlusion removal system 100 facilitates removal of occlusive aggregate in the blood by filtering the aggregate from the blood and returning the blood to the blood stream. This type of operation can advantageously be accomplished as part of a single, continuous cutting and removal process, according to various embodiments.

In some embodiments, the catheter system 110 can be coupled to the control handle 120 via a drive shaft (not shown in FIG. 1) extending from within the control handle 120 for controlling certain aspects of the catheter system 110 during operation. The control handle 120 is also usable to position the catheter system 110 inside the body lumen from which occlusive material is to be removed.

As shown, the occlusion removal system 100 can also optionally include an outer sheath 200 coupled to the control handle 120 and disposed over at least a portion of the catheter system 110. In some embodiments, the valve 140 is located on the outer sheath 200.

In some embodiments, the outer sheath 200 defines a lumen having a proximal end 200a (not shown) and a distal end 200b. The outer sheath 200 is configured to receive a proximal end 20 of the catheter body 10. In some embodiments, the outer sheath 200 may be an appropriate length to extend over at least a portion of the catheter body 10. For example, the outer sheath may extend over one or more filtration sections 30 of the catheter body 10 such that the outer sheath 200 is operable to contain or store filtered blood during operation of the catheter system 110. In other embodiments, the outer sheath 200 may extend over one or more portions of the catheter body 10 to aid in controlling the location of blood flow into and/or out of the catheter system 110 (e.g., by selectively covering or revealing portions of the one or more filtration sections 30).

In some embodiments, the outer sheath 200 is movable longitudinally over an outer surface 25 of the catheter body 10. For example, the outer sheath 200 may be movable in a proximal direction and/or distal direction to expose a desired length of the catheter body 10. In some examples, a fluid, such as a saline solution, can be injected into the catheter body 10, catheter system 110, or remove occlusive material from within the catheter body 10.

Figure 2:
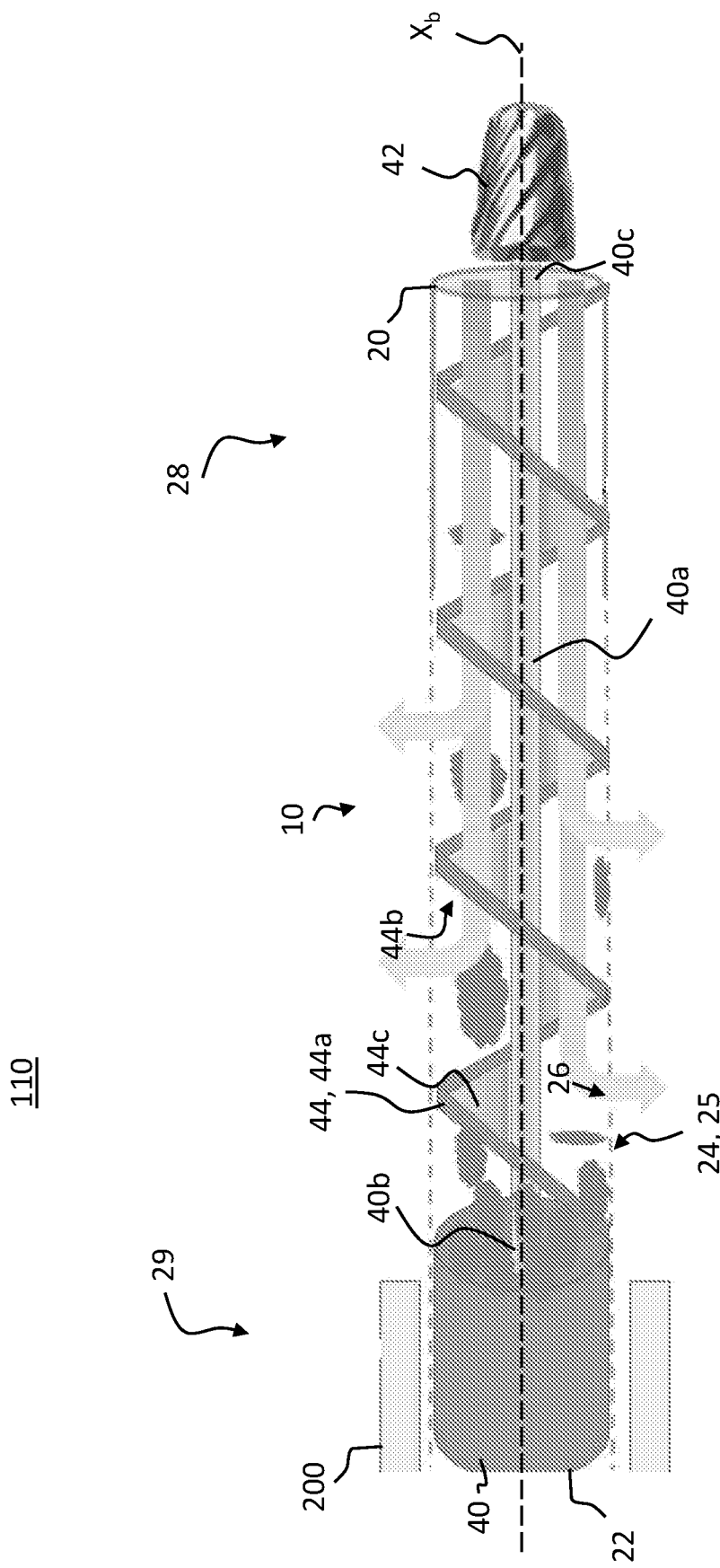
FIG. 2 illustrates a catheter system, according to some embodiments.

FIG. 2 shows the catheter system 110, according to some embodiments. As shown, the catheter system 110 includes a catheter body 10 control handle 120 and a cutter assembly 12 within the catheter body 10.

In some embodiments, the catheter body 10 extends between a distal end 20 and a proximal end 22, defines a central axis Xb, and includes a wall 24 that defines an outer surface 25 and an inner surface 26, the inner surface 26 forming a lumen. The catheter body 10 includes a distal portion 28 toward the distal end 20 and a proximal portion 29 toward the proximal end 22. The distal end 20 is optionally described as a working end or a terminal end.

In some embodiments, the distal portion 28 includes one or more filtration portions 30, including a filtration section 30a, and one or more impermeable sections 34, including a first impermeable section 34a and a second impermeable section 34b. Generally, the one or more filtration portions 30 of the catheter body 10 are configured to permit fluids (e.g., blood) to pass while filtering or otherwise inhibiting passage of occlusive aggregate (e.g., debris from broken plaque deposits, thrombosis material, or other particulate in the body lumen) through the filtration section 30a. In turn, the one or more impermeable sections 34 are generally configured to be less permeable to occlusive aggregate or inhibit passage of fluids, such as blood, and occlusive aggregate altogether.

Figure 3:
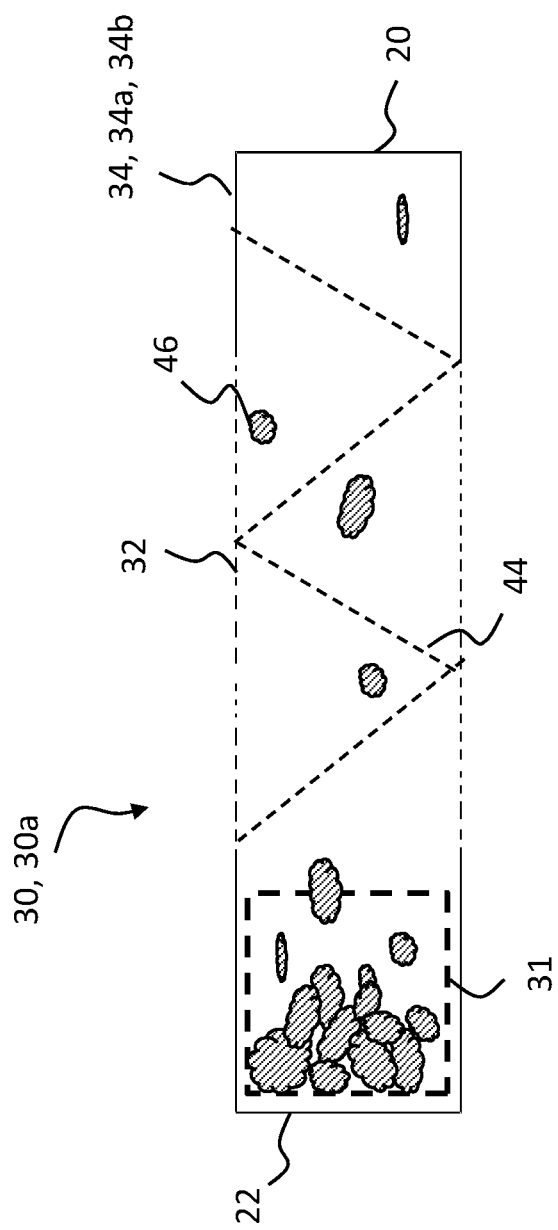
FIG. 3 is a close-up view of a filtration section within the catheter system, according to some embodiments.

FIG. 3 shows a close-up view of the filtration section 30a including a filter media 32. In some embodiments, the filter media 32 is configured to permit blood to pass through the filter media 32, while inhibiting or preventing occlusive aggregate from passing during operation of the catheter system 110.

In some examples, the filter media 32 is configured to permit fluid (e.g., blood) to pass in one direction, from inside the catheter body 10, through the wall 24, outside of the catheter body 10, and to inhibit or prevent fluid (e.g., blood)

from passing in the reverse direction (i.e., outside-in). In other examples, the filter media 32 is configured to permit fluid (e.g., blood) to flow in either direction through the wall 24, depending upon a pressure differential between the inner surface 26 and the outer surface 25 at the filtration section 30a.

In turn, according to various embodiments, the filter media 32 is configured to inhibit, or prevent occlusive aggregate (e.g., debris from broken up occlusive material such as plaque or thromboses) from passing through the wall 24 at the filtration section 30a. The filter media 32 may be formed of a variety of suitable materials, but in some examples is formed of a biocompatible material such as metallic foils or meshes, or sheets or meshes formed of polymeric materials, such as a fluoropolymer (e.g., expanded polytetrafluoroethylene, or ePTFE and composites thereof). In some examples, a filter media 32 is formed by laser perforating one or more layers of a thin, polytetrafluoroethylene (PTFE) membrane. Some suitable examples of materials for use as the filter media 32 are described in US 2003/0187495, entitled "Endoluminal Devices, embolic filters, methods of manufacture and use" and filed Apr. 1, 2002 by W.L. Gore and Associates, and US 2004/0093012, entitled "Embolic filter frame having looped support strut elements" and filed Oct. 17, 2002 by W. L. Gore and Associates.

In some embodiments, the filter media 32 is configured similarly to embolism filter media capable of trapping occlusive aggregate 46 inside the catheter body 10. The filter media 32 should also permit blood to move from the catheter body 10 back into the bloodstream (i.e. body lumen). In various embodiments, the filter media 32 may be reinforced (e.g., with one or more reinforcement layers or reinforcement members) to help the filter media 32 maintain its form during use of the catheter system 110.

In some examples, a microstructure of the filter media 32 (e.g., node and fibril structure in the case of ePTFE) serves to provide the filtration function previously described. Additionally or alternatively, the filter media 32 may include suitably-sized apertures, folds, pleats, or other features for modifying the permeability of the filter media 32, such as modifying the type and size of occlusive aggregate permitted to pass through the filter media 32 and/or the rate of diffusion through the filter media 32.

In some embodiments, the filter media 32 includes one or more coatings, surface treatments, or modifications with therapeutic agents to enhance performance. For example, in some embodiments, the filtration section 30 includes a coating or surface treatment of heparin, such as the heparin bioactive surface treatment provided under the tradename "CBAS" by Carmeda AG. Such surface treatments may help slow or prevent fouling of the filter media 32 during operation of the catheter system 110.

As is understood by those in the field, the overall permeability of a material is impacted by such variables as pressure differential across a material sample, the permeant being evaluated, and the time for diffusion across the sample. In the context of the present disclosure, permeability may be assessed using ASTM standards selected based upon the material being evaluated. In one example, the filter media 32 is permeable to fluid (e.g., blood) at a pressure sufficient to return the fluid to the bloodstream. In some examples, the filter media 32 is permeable to fluid at least at pressures of 10 mmHg, 20 mmHg, 50 mmHg, 100 mmHg, greater than 100 mmHg, or other value as desired, over a desired time period, such as at least 30 seconds or 30 minutes, for example. In turn, according to various examples, the filter media 32 at similar pressures and for similar time periods is impermeable to occlusive aggregate (e.g., plaque or thrombosis debris) having a size of 100 micrometers or greater, 200 micrometers or greater, 300 micrometers or greater, 500 micrometers or greater, or other sizes as desired.

Each of the one or more impermeable sections 34 can be similar, although one or more impermeable sections 34 with differing properties (e.g., permeability properties) are contemplated. In some embodiments, the first impermeable section 34a is located between the distal end 20 and the filtration section 30a while the second impermeable section 34b is located between the filtration section 32a and the proximal end 22. As referenced, the one or more impermeable sections 34 are generally impermeable to fluids such as blood, for example, and may prevent fluid from exiting the catheter before entering the filtration section 30a and/or contacting filter media 32. In some examples, the one or more impermeable sections 34 are impermeable to fluid (e.g., blood) at pressures of 10 mmHg, 20 mmHg, 50 mmHg, 100 mmHg, greater than 100 mmHg, or other value as desired, over a desired time period, such as at least 30 seconds or 30 minutes, for example.

In some embodiments, the filtration section 30a of the catheter body 10 is defined as a continuous portion of the catheter body 10 that extends continuously along a segment of the length of the catheter body 10 about an entire circumference of the catheter body 10. For example, a continuous, circumferential portion of the wall 24 of the catheter body 10 is optionally formed of material that is configured to have a desired permeability to fluid yet be impermeable to occlusive aggregate. In some embodiments, the filtration section 30a may extend continuously along greater than 50% of the catheter body 10. In other embodiments, the filtration section 30a may extend along the entire length of the catheter body 10. In yet other embodiments, the filtration section 30a is comprised of multiple, discrete portions of the wall 24 that are separated longitudinally, along the length of the catheter body 10, and/or that are separated circumferentially about the circumference of the catheter body 10.

Each of the one or more filtration portions 30 can be similar to those discussed above, although multiple filtration portions 30 with differing configurations are contemplated. Although various options for the filtration section 30a are described, and only a single filtration section (i.e., the filtration section 30a) is shown in FIG. 2, it should be understood that in instances where multiple filtration sections are employed, any of the features described in association with the filtration section 30a are applicable to the one or more filtration portions 30 as desired.

As shown in FIG. 2, the cutter assembly 12 includes a drive mechanism 40, a cutter 42, and a conveyor 44, according to some embodiments. The cutter assembly 12 is received in and maintained by the catheter body 10. In general terms, the drive mechanism 40 is rotatable within the lumen of the catheter body 10 and is coupled to the cutter 42 and the conveyor 44 for rotating the cutter 42 and the conveyor 44 during a cutting operation.

In some embodiments, the drive mechanism 40 includes a shaft 40a that extends longitudinally within the catheter body 10, for example along the longitudinal axis Xb, and defines a proximal end 40b and a distal end 40c. In various examples, the drive mechanism 40 extends from the proximal end 22 of the catheter body 10 to the distal end 20 of the catheter body 10.

In some embodiments, the cutter 42 is configured as a burr or other cutting implement and is coupled to the distal end 40c of the shaft 40a, such that rotation of the shaft 40a translates to rotation of the cutter 42. As shown, at least a portion of the cutter 42 projects distally from the catheter body 10 (e.g., for engaging occlusive material in a body lumen during a cutting operation). In some embodiments, the conveyor 44 is configured as a screw conveyor, also described as an auger conveyor or an impeller. As shown, the conveyor 44 includes a rotatable, helical screw blade 44a configured to move liquid (e.g., blood) and occlusive aggregate proximally. In some embodiments, the conveyor 44 contacts the filtration section 30a to define spaces configured to trap the occlusive material between the conveyor 44 and the filtration section 30a as the occlusive material is conveyed within the catheter body 10.

In some examples, the helical screw blade 44a includes an edge portion 44b and a web portion 44c. The edge portion 44b is formed of a suitable material (e.g., a polymeric or metallic material). In some embodiments, the cutter assembly 12 is self-expandable from a first diametric profile to a second, larger diametric profile to fit a body lumen. For example, the edge portion 44b may be configured to be expandable or self-expanding (e.g., being formed of an elastic material such as stainless steel or a shape-memory material such as nitinol). In some examples, the web portion 44c is also configured to expand with the edge portion 44b. For example, the web portion 44c may be formed of a similar material to the edge portion 44b and/or may be formed of a material with recovery properties, such as ePTFE. Some suitable examples of expandable impellers are described in US 2009/0198219, entitled "Catheter Assembly" and filed Apr. 14, 2009 by W.L. Gore and Associates. In some embodiments, the web portion 44c may be angled such that occlusive aggregate 46 contacting the web portion 44c is directed radially outward toward the filter media 32.

In some embodiments, the drive mechanism 40 is configured to rotate either the cutter 42, the conveyor 44, or both the cutter 42 in combination with the conveyor 44, the cutter 42 being coupled to the distal end 40c of the shaft 40a. The drive mechanism 40 may be powered by an electric motor operatively coupled to the drive mechanism 40 or, in some embodiments, located within the control handle 120. In some embodiments, the rotational speed of the shaft 40a, and the conveyor 44 and/or the cutter 42 is adjustable via the control handle 120. As is known in the art, the desired rotational speed may depend on the configuration of the conveyor 44, the cutter 42 and/or various properties of the occlusive material. However, in some embodiments, the shaft 40a and conveyor 44 and/or cutter 42 are rotatable at speeds up to about 100 RPMs (rotations per minute), 500 RPMs, 1,000 RPMs, 10,000 RPMs, 20,000 RPMs, or greater than 20,000 RPMs for example, although a variety of speeds are contemplated.

Figure 4:
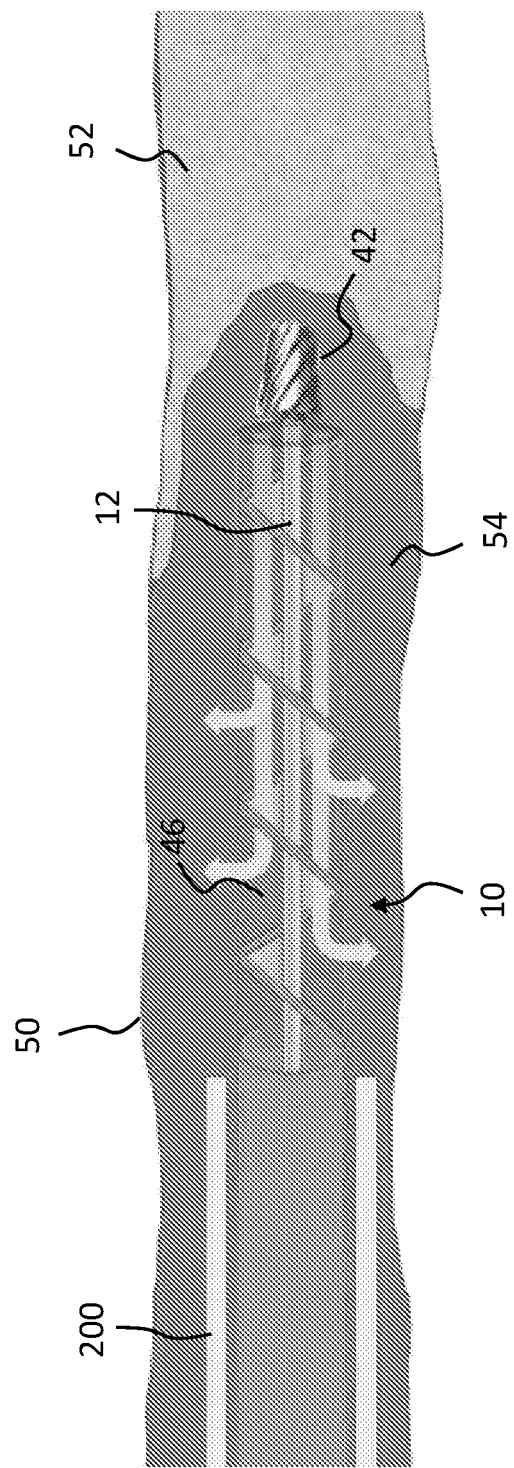
FIG. 4 shows the catheter system of FIG. 2 deployed in a body vessel during an occlusion removal process, according to some embodiments.

FIG. 4 shows the catheter system 110 during one exemplary use within a body lumen 50. The catheter body 10 is introduced into a body lumen 50 to a desired treatment site. An example of a desired treatment site includes, but is not limited to, areas of vascular occlusion within arteries, veins, airways, gastrointestinal passages, biliary system passages, and other body conduits. Once proximate the occlusion 52, rotation of the cutter assembly 12 is activated via the drive mechanism 40 and applied to the occlusion 52. In some embodiments, the rotational speed of the cutter 42 is adjustable. The occlusion 52 is cut, or otherwise macerated, grinded, sanded, etc., creating loose, free-moving occlusive aggregate 46. As the cutter assembly 12 rotates, a pressure differential is generated within the body lumen 50 and the occlusive aggregate 46 is drawn into the catheter body 10 along with surrounding body fluid 54 (e.g., blood). The body fluid 54 is permitted to return to the body lumen 50 through the filter media 32, while the occlusive aggregate 46 is conveyed proximally through the catheter body 10.

In some embodiments, the occlusive aggregate 46 is accumulated in a retention portion 31 (FIG. 3) of the filtration section 30a of the catheter body 10 during operation. For example, the occlusive aggregate 46 may enter through a distal end 40c of the catheter body 10 and be conveyed proximally through the catheter body 10 away from the cutter assembly 12 and into the retention portion 31. In some embodiments, the retention portion 31 may be located at the proximal end of the catheter body 10. In other embodiments, the occlusive aggregate 46 may also accumulate in the conveyor 44 or any other part of the catheter body 10.

In some embodiments, the retention portion 31 may be one of a bag, a sack, a mesh, or any other type of enclosed portion. The occlusive aggregate 46 captured in the retention portion 31 may be retained within the retention portion 31 until removal of the catheter body 10 from the patient. In other embodiments, the occlusive aggregate 46 captured in the retention portion 31 may be continually removed during operation.

The occlusive aggregate 46 can be removed from the catheter body 10 by way of fluid injection at a location along the catheter body 10. In some embodiments, fluid is injected at either the distal end 20 or proximal end 22 of the catheter body. In some embodiments, the fluid is introduced into the catheter body 10 through a valve or port near the proximal end 22 of the catheter body 10. In some embodiments, a delivery tube 160 may be attached to the valve 140 at a distal end. The fluid may be injected into the delivery tube 160 at a proximal end of the delivery tube 160. For example, the fluid may be delivered with a syringe, or other fluid-injection means. The volume of fluid delivered is dependent on the size of the catheter system 110 and the amount of flushing required, for example. The fluid may include a normal saline solution, heparinized saline solution, or any other appropriate flushing solution known to those skilled in the art.

In some embodiments, the outer sheath 200 is extended longitudinally along the outer surface 25 of the catheter body 10 to cover the filtration section 30a, filter media 32, the retention portion 31, and/or the conveyor 44 to permit fluid to be injected into the lumen of the outer sheath 200 to flush fluid and occlusive debris into the conveyor 44 for cleaning purposes. In some embodiments, the outer sheath 200 may be retracted a desired amount to expose the one or more filtration portions 30. In one example, the outer sheath 200 may slide over the filter media 32 to the distal end 20 of the catheter body 10 and create a tight seal. In some embodiments, fluid may be injected at a location along the outer sheath 200 and generate a pressure differential in a proximal direction such that occlusive debris may be removed/flushed in the proximal direction. In some examples, this allows for the removal of occlusive debris from the catheter body 10 while the catheter body 10 remains in the body of a patient.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A catheter system for removal of occlusive material in a body lumen, the system comprising:
   a catheter body having a lumen, and extending between a distal end and a proximal end, the catheter body having a distal portion and a proximal portion, the distal portion including a filtration section including a filter media configured to perm it blood to pass from the lumen of the catheter body and to inhibit occlusive material from passing out of the lumen of the catheter body;
   a control handle coupled to the proximal portion of the catheter body; and
   a cutter assembly including,
      a drive mechanism extending between the proximal portion and the distal portion of the catheter body, the drive mechanism being operatively connected to the control handle; and
      a conveyor extending within the distal portion of the catheter body, the conveyor being coupled to the drive mechanism such that the conveyor is rotatable with the drive mechanism to convey the occlusive material from the body lumen proximally within the catheter body and through the filtration section such that blood is permitted to pass from the lumen of the catheter body and the occlusive material is inhibited from passing out of the lumen of the catheter body and is conveyed proximally within the lumen of the catheter body; and
      an outer sheath having a lumen and configured to extend over the filtration section such that fluid is deliverable through the lumen of the outer sheath to flush the occlusive material out of the cutter assembly by introducing the fluid into the lumen of the catheter body and rotating the conveyor.

2. The system of claim 1, wherein the cutter assembly includes a cutter configured to cut occlusive material, the cutter extending from the distal end of the catheter body and being coupled to the drive mechanism such that the cutter is rotatable with the drive mechanism to cut occlusive material.

3. The system of claim 2, wherein the cutter includes one or more burr elements and the conveyor includes one or more screw elements and/or impeller elements.

4. The system of claim 1, wherein the filter media comprises ePTFE.

5. The system of claim 1, wherein the filtration section defines a portion of the lumen of the catheter body, and further wherein the conveyor contacts the filtration section to define spaces configured to trap the occlusive material between the conveyor and the filtration section as the occlusive material is conveyed within the catheter body.

6. The system of claim 1, wherein the cutter assembly includes a cutter and the drive mechanism includes an electric motor and a shaft operatively coupling the electric motor to at least one of the conveyor and the cutter.

7. The system of claim 1, wherein the distal portion of the catheter body further comprises an impermeable section between the distal end of the catheter body and the filtration section, the impermeable section being impermeable to fluid.

8. The system of claim 1, wherein the cutter assembly is self-expandable from a first diametric profile to a second, larger diametric profile to fit a body lumen.

9. The system of claim 1, wherein the cutter assembly includes a self-expanding frame formed of a shape-memory material.

10. A method of removing occlusive material from a body lumen of a patient, the method comprising:
    intraluminally delivering the catheter system of claim 1 to a desired treatment site in the body lumen of the patient; and
    activating rotation of the cutter assembly proximate the occlusive material in the body lumen at a speed adequate to produce a pressure drop, causing the occlusive material to be drawn into the distal end of the catheter body and conveyed proximally within the catheter body while blood is permitted to return to the body lumen through the filter media of the filtration section as the occlusive material is conveyed proximally.

11. A catheter system for removal of occlusive material in a body lumen, the system comprising:
    a catheter body having a lumen, and extending between a distal end and a proximal end, the catheter body having a distal portion and a proximal portion, the distal portion including a filtration section including a filter media configured to permit blood to pass from the lumen of the catheter body and to inhibit occlusive material from passing out of the lumen of the catheter body, the distal portion further including an impermeable section between the distal end of the catheter body and the filtration section, the impermeable section being impermeable to fluid;
    a control handle coupled to the proximal portion of the catheter body; and
    a cutter assembly including:
       a drive mechanism extending between the proximal portion and the distal portion of the catheter body, the drive mechanism being operatively connected to the control handle; and
       a conveyor extending within the distal portion of the catheter body, the conveyor being coupled to the drive mechanism such that the conveyor is rotatable with the drive mechanism to convey the occlusive material from the body lumen proximally within the catheter body and through the filtration section such that blood is permitted to pass from the lumen of the catheter body and the occlusive material is inhibited from passing out of the lumen of the catheter body and is conveyed proximally within the lumen of the catheter body.

12. The system of claim 11, wherein the cutter assembly includes a cutter configured to cut occlusive material, the cutter extending from the distal end of the catheter body and being coupled to the drive mechanism such that the cutter is rotatable with the drive mechanism to cut occlusive material.

13. The system of claim 12, wherein the cutter includes one or more burr elements and the conveyor includes one or more screw elements and/or impeller elements.

14. The system of claim 11, wherein the filter media comprises ePTFE.

15. The system of claim 11, further comprising an outer sheath having a lumen and configured to extend over the filtration section such that fluid is deliverable through the lumen of the outer sheath to flush the occlusive material out of the cutter assembly by introducing the fluid into the lumen of the catheter body and rotating the conveyor.

16. The system of claim 11, wherein the filtration section defines a portion of the lumen of the catheter body, and further wherein the conveyor contacts the filtration section to define spaces configured to trap the occlusive material between the conveyor and the filtration section as the occlusive material is conveyed within the catheter body.

17. The system of claim 11, wherein the cutter assembly includes a cutter and the drive mechanism includes an electric motor and a shaft operatively coupling the electric motor to at least one of the conveyor and the cutter.

18. The system of claim 11, wherein the cutter assembly is self-expandable from a first diametric profile to a second, larger diametric profile to fit a body lumen.

19. The system of claim 11, wherein the cutter assembly includes a self-expanding frame formed of a shape-memory material.

20. A method of removing occlusive material from a body lumen of a patient, the method comprising:
intraluminally delivering the catheter system of claim 11 to a desired treatment site in the body lumen of the patient; and
activating rotation of the cutter assembly proximate an occlusive material in the body lumen at a speed adequate to produce a pressure drop, causing the occlusive material to be drawn into the distal end of the catheter body and conveyed proximally within the catheter body while blood is permitted to return to the body lumen through the filter media of the filtration section as the occlusive material is conveyed proximally.

* * * * *